United States Patent [19]

Yamamura et al.

[11] 4,243,492

[45] Jan. 6, 1981

[54] PROCESS FOR PURIFYING CRUDE OLEFIN OXIDES

[75] Inventors: Toshio Yamamura; Yoshiro Osawa; Isao Ouchi; Nobuteru Oda; Mitsuyoshi Yamazaki; Yukio Nishiyama, all of Yokohama, Japan

[73] Assignee: Showa Denko K.K., Japan

[21] Appl. No.: 849,535

[22] Filed: Nov. 8, 1977

[30] Foreign Application Priority Data

Nov. 15, 1976 [JP] Japan .................................. 51/136338

[51] Int. Cl.$^3$ ...................... B01D 3/34; C07D 301/32
[52] U.S. Cl. ......................................... 203/8; 203/50; 260/348.37
[58] Field of Search .................. 203/8, 50; 260/348.37

[56] References Cited

U.S. PATENT DOCUMENTS 2,622,060  12/1952  Robeson et al. ................. 260/348.37

FOREIGN PATENT DOCUMENTS 2108922  8/1972  Fed. Rep. of Germany ...... 260/348.37
2435821  2/1976  Fed. Rep. of Germany .

OTHER PUBLICATIONS

Translation of German Offenlegungschrift, No. 2,108,922.

Primary Examiner—Hiram H. Bernstein
Attorney, Agent, or Firm—Wenderoth, Lind & Ponack

[57] ABSTRACT

A crude olefin oxide containing high-boiling ingredients is distilled at a pH of 4 to 7 in the presence of a nonvolatile neutral or weakly basic alkali metal or alkaline earth metal salt or hydroxide to separate the olefin oxide from the high-boiling ingredients. This permits the prevention of the polymerization of the olefin oxide and its conversion to the corresponding glycol.

7 Claims, No Drawings

PROCESS FOR PURIFYING CRUDE OLEFIN OXIDES

This invention relates to a process for purifying crude olefin oxides containing high-boiling ingredients, and more specifically, to a process for separating the olefin oxides from the high-boiling ingredients by distillation.

An olefin oxide such as ethylene oxide, propylene oxide or butylene oxide is currently prepared by a "chlorohydrin process" which comprises reacting the corresponding olefin with chlorine in the presence of water to form an olefin chlorohydrin, and then adding an alkaline substance to the resulting reaction solution to saponify the chlorohydrin; or a "direct oxidizing process" which comprises oxidizing the olefin with molecular oxygen or peroxides. Both of these methods cannot avoid the formation of by-product impurities having higher boiling points than the intended olefin oxide. These high-boiling ingredients and water present in the reaction mixture are separated generally by distillation. Very frequently, however, the olefin oxide is converted to a glycol or polymerizes during the distillation to cause losses of the olefin oxide formed. Furthermore, this hampers the safety of the distillation operation or causes the corrosion of the distillation apparatus.

It is an object of this invention to provide a process for separating high-boiling ingredients from a crude olefin oxide efficiently by distillation without involving the difficulties described hereinabove.

The process of this invention is described in detail below with particular reference to crude propylene oxide obtained by the chlorohydrin method.

Propylene oxide in this case is produced by reacting propylene with chlorine in the presence of water to form propylene chlorohydrin, and adding an alkaline substance such as sodium hydroxide, sodium carbonate or calcium hydroxide to saponify the propylene chlorohydrin. The reactions are schematically shown as follows:

$$CH_2=CHCH_3 + Cl_2 + H_2O \longrightarrow CH_3 \cdot CHOH \cdot CH_2Cl + HCl \quad (1)$$

$$2CH_3 \cdot CHOH \cdot CH_2Cl + Ca(OH)_2 \longrightarrow$$

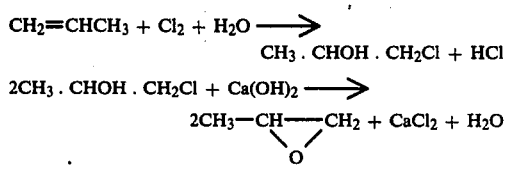

$$2CH_3-CH\underset{O}{\overset{}{-\!-\!-}}CH_2 + CaCl_2 + H_2O \quad (2)$$

In the saponification step, propylene oxide is stripped by blowing steam as it is formed, and is taken out as contained in the effluent. The effluent is an aqueous solution usually containing about 70 to 80% of propylene oxide. As impurities, it contains certain amounts of the unreacted propylene chlorohydrin, and of by-products in the chlorohydrin-forming step and the saponifying step such as propionaldehyde, propylene dichloride and dichlorodiisopropyl ether. The water, propylene chlorohydrin, and the by-products all have higher boiling points than the boiling point (34° to 35° C.) of propylene oxide. The crude propylene oxide containing such high-boiling ingredients is then distilled, and propylene oxide separated from the high-boiling ingredients including water is taken out from the top of the distillation tower. The top fraction, if desired, may be further purified by using one or more fractional distillation towers.

In the conventional distillation step for the crude propylene oxide, it is inevitable that a part of propylene oxide is hydrated to propylene glycol which is conducted to the tower bottom together with the other high-boiling ingredients and withdrawn from there. Hence, the conventional technique presents difficulties such as the loss of propylene oxide and the increase of COD (chemical oxygen demand) of the effluent from the distillation step. It is possible to separate the effluent from the bottom of the distillation tower into an aqueous layer and an oil layer and recover the propylene glycol for reuse by distilling the water layer. This procedure, however, is undesirable because it requires additional equipment and costs.

Accordingly, the basic need would be to inhibit the conversion of propylene oxide to propylene glycol during the distillation of crude propylene oxide. This is by no means easy as will be described below. Conversion of propylene oxide to propylene glycol is promoted when the temperature is higher, the time of contact of propylene oxide with water is longer, and the pH of the solution is lower (for example, when the pH is below 4). Hence, the first thing which those skilled in the art would do to inhibit the hydration reaction of propylene oxide during the distillation is to perform the distillation at low temperatures under reduced pressure. Such a method, however, requires a special device for maintaining the distillation system at reduced pressure, and the pressure reduction causes the loss of propylene oxide and the increase of the amount of a cooling energy. The next thing conceivable will be to elevate the temperature of the distillation system to shorten the residence time of propylene oxide and the time of contact with water. However, elevated temperatures promote the thermal decomposition of organic chlorine compounds such as propylene chlorohydrin or propylene dichloride and lead to the evolution of hydrogen chloride. Consequently, various difficulties are caused. For example, the pH is further reduced and the formation of the glycol is promoted. Or the equipment undergoes corrosion. The third measure which can be suggested to avoid low pH values is to perform the distillation in the presence of an alkaline substance such as sodium hydroxide added to the distillation system. However, under alkaline conditions, propylene oxide readily polymerizes, and its loss is inevitable. At a pH of more than about 12, the polymerization reaction takes place vigorously, and the generated heat of polymerization promotes the polymerization to cause a danger of explosion. Moreover, under strongly alkaline conditions, the dichlorodiisopropyl ether present decomposes to form monochloropropene having a boiling point close to that of propylene oxide, which adversely affects the purity of the propylene oxide product.

To the best of our knowledge and belief, there has been no method which can satisfactorily overcome these various difficulties associated with the distillation of crude propylene oxide. The present invention provides a method for efficiently separating propylene oxide from high-boiling ingredients without involving such difficulties.

The process for purifying a crude olefin oxide containing high-boiling ingredients in accordance with this invention comprises distilling the crude olefin oxide in the presence of an additive selected from the group consisting of neutral to weakly basic inorganic acid salts of alkali metals or alkaline earth metals and hydroxides of alkaline earth metals, said additive being added in an amount sufficient to maintain the pH of the liquid phase in the distillation system at 4 to 7, and separating the olefin oxide from the high-boiling ingredients.

Specific examples of the additive include NaCl, Na$_2$CO$_3$, NaHCO$_3$, Na$_2$SO$_3$, NaHSO$_3$, Na$_2$SO$_4$, NaHSO$_4$, CaCl$_2$, CaCO$_3$, Ca(OH)$_2$, and mixtures of these.

These additives are nonvolatile neutral to weakly basic compounds. NaCl and Na$_2$SO$_4$ are neutral salts of alkali metals, and NaCl is especially preferably used as the additive in the present invention.

According to the present invention, the additive is used in an amount sufficient to maintain the pH of the liquid phase of the distillation system at 4 to 7, and the distillation is carried out in the presence of the additive. Without the additive, hydrogen chloride evolved by the decomposition of chlorine-containing organic impurities described hereinabove would acidify the liquid phase of the distillation system in the distillation column, especially at its bottom, and the pH of the liquid phase would decrease to an undesirable degree. The crude propylene oxide solution obtained by the direct oxidizing method shows an undesirable pH by organic acid impurities formed as by-products during the oxidation. The additive used in this invention serves to maintain the pH of the liquid phase of the distillation system at 4 to 7.

It seems strange that neutral additives, for example neutral salts such as NaCl or Na$_2$SO$_4$, are useful for pH adjustment. Such an effect is believed to be due to the formation of NaOH by the reaction of the neutral salts with a very small amount of propylene oxide as schematically shown below.

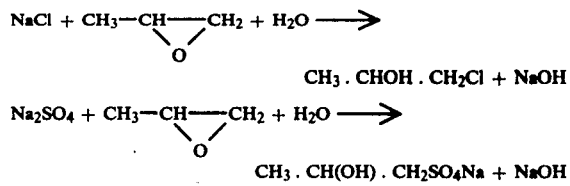

The reactions expressed by these equations are very slight, and the amount of propylene oxide consumed by these reactions is only a trace amount which can be neglected. These additives seem to act as if they were a buffer agent, and depending upon the amount of the acid component in the liquid phase, form NaOH in an amount sufficient to neutralize the acid. Hence, there is no likelihood of excessively increasing the pH of the liquid phase. Of course, it is not likely that these neutral salts increase the pH of the liquid phase excessively at certain localities as does sodium hydroxide directly added.

The amount of the additive somewhat varies according to the composition of the crude propylene oxide solution to be distilled. Generally, the amount of the additive is as small as 0.01 to 0.2% by weight based on the amount of water in the crude propylene oxide feed stock. The additive can be added to the crude feed stock, or to the column or bottom of the distillation tower.

The following Examples illustrates the present invention in more detail.

EXAMPLE 1

Milk of lime was added to an aqueous solution of propylene chlorohydrin (PCH for short), and PCH was saponified while passing steam. The saponified product was subjected to a gas-liquid separator, and the effluent crude propylene oxide (PO) solution was separated by a multi-tray rectifying tower under the following conditions.

Pressure: atmospheric pressure
Temperature: bottom 85° to 90° C., top 35° C.
Reflux ratio: about 3.5

The crude feed stock was fed to the middle stage of the tower. Propylene oxide (PO) distilled out from the top of the column, and high-boiling ingredients such as propylene dichloride (PDC), dichlorodiisopropyl ether (DCIP), propylene glycol (PG), propionaldehyde (PA), PCH, and water and at times dipropylene glycol (DPG) distilled out from the bottom. The effluent from the bottom was allowed to stand in a decanter to separate it into an aqueous layer and an oil layer.

NaCl was used as an additive in the form of an aqueous solution having a concentration of about 10% by weight. It was added in an amount corresponding to 0.1% by weight based on the amount of the aqueous layer to the bottom or between the bottom and feed stage of the distillation tower.

The crude propylene oxide solution was thus continuously distilled, and the results are shown in Table 1. In Table 1, (A) refers to the case of using no additive; (B), to the case of adding NaCl to the bottom of the tower; and (C), to the case of adding NaCl between the bottom and the feed stage of the distillation tower.

TABLE 1

| NaCl | Feed stock | Bottom fraction | | | Top fraction | | |
|---|---|---|---|---|---|---|---|
| | | A | B | C | A | B | C |
| Flow rate (T/D) | — | 0 | 0.16 kg/h | 0.16 kg/h | — | — | — |
| | 26.7 | 6.7 | 6.0 | 6.0 | 20 | 20.8 | 20.9 |
| Composition | wt. % | wt. % | wt. % | wt. % | wt. % | wt. % | wt. % |
| PO | 76.86 | 0.7 | 0.7 | 0.7 | 100 | 100 | 100 |
| PA | 0.17 | 0.7 | 0.7 | 0.7 | 15 ppm | 15 ppm | 15 ppm |
| PDC | 6.60 | 26.0 | 27.9 | 27.9 | — | — | — |
| PCH | 0.57 | 2.3 | 2.4 | 2.4 | — | — | — |
| DCIP | 1.08 | 4.3 | 4.6 | 4.6 | — | — | — |
| PG | 0.02 | 9.1 | 0.1 | 0.1 | — | — | — |
| DPG | — | 0.1 | — | — | — | — | — |
| H$_2$O | 14.70 | 56.8 | 62.7 | 62.7 | 30 ppm | 30 ppm | 30 ppm |
| pH | ca. 7 | 3.3 | 6.0 | 6.0 | — | — | — |
| PG conversion (%) | — | 2.1 | 0.2 | 0.2 | — | — | — |

As is seen from the results given in Table 1, the conversion of PO to PG in the distillation tower can be drastically reduced by the presence of NaCl in the distillation tower. Hence, the amount of PO obtained increases, and the amount of PG in the bottom fraction (aqueous layer) decreases. Thus, the COD load in the treatment of the effluent decreases from 130,000 ppm to 20,000 ppm, and the cost of operation is reduced. Since the bottom fraction is nearly neutral, it naturally contributes to the prevention of corrosion of the equipment. The effect of the additive has been found to be almost the same whether it is added to the bottom or to the middle stage of the distillation tower.

EXAMPLE 2

The crude propylene oxide solution was distilled in the same way as in Example 1 except that the type and amount of the additive to be added to the distillation system were changed. The conversion of PO to PG in the distillation tower was determined, and the results are shown in Table 2.

TABLE 2

| Type of additive | Amount of the additive (wt. %)* | pH of the bottom fraction | Conversion of PO to PG (%) |
|---|---|---|---|
| Not added | — | 3.50 | 1.77 |
| Not added | — | 4.0 | 1.82 |
| NaCl | 0.015 | 4.21 | 0.48 |
|  | 0.05 | 4.04 | 0.27 |
|  | 0.09 | 4.77 | 0.14 |
|  | 0.10 | 4.35 | 0.15 |
| $Na_2CO_3$ | 0.06 | 4.9 | 0.19 |
|  | 0.075 | 5.0 | 0.13 |
|  | 0.13 | 6.8 | 0.16 |
| $Na_2SO_3$ | 0.11 | 4.01 | 0.87 |
|  | 0.11 | 4.20 | 0.39 |
|  | 0.16 | 4.90 | 0.37 |

*Amount based on the amount of the aqueous layer of the bottom fraction. Almost the same effect was obtained when $NaHCO_3$, $NaHSO_3$, $NaHSO_4$, $Na_2SO_4$ or $Ca(OH)_2$ was used.

As demonstrated by the above specific working examples, the addition of a small amount of the additive to the crude propylene oxide solution serves to maintain the pH of the liquid phase of the distillation system at 4 to 7, and permits a very effective inhibition of the conversion of propylene oxide to propylene glycol. According to the present invention, therefore, it is not necessary to reduce the pressure of the distillation system or to heat it to particularly high temperatures, and by distilling the crude propylene oxide solution under usual distillation conditions, the loss of the propylene oxide can be minimized. Moreover, the operation can be performed safely and smoothly.

While the process of the invention has been described with reference to the distillation of crude propylene oxide obtained by the chlorohydrin method, it should be understood that the present invention can be effectively applied also to the crude product containing high-boiling organic acids which is obtained by the direct oxidizing method, and to other olefin oxides such as ethylene oxide or butylene oxide.

What we claim is:

1. In a process for purifying a crude olefin oxide containing high-boiling ingredients by ordinary fractional distillation, the improvement which consists essentially of distilling the crude olefin oxide in the presence of an additive selected from the group consisting of NaCl and $Na_2SO_4$ said additive being added in an amount sufficient to maintain the pH of the liquid phase in the distillation system at 4 to 6.8, and separating the olefin oxide from the high-boiling ingredients.

2. The process of claim 1 wherein the olefin oxide is ethylene oxide, propylene oxide or butylene oxide.

3. The process of claim 1 wherein the crude olefin oxide is crude propylene oxide obtained by reacting chlorine with propylene in the presence of water, saponifying the resulting aqueous solution of propylene chlorohydrin with an alkaline compound, and stripping the saponified product.

4. The process of claim 1 wherein the additive is added to the crude olefin oxide feed stock and is present as dissolved therein.

5. The process of claim 1 wherein the additive is added in the form of an aqueous solution to the distillation system, and is present in the liquid phase of the distillation system.

6. The process of claim 1 wherein the distillation is performed in a distillation tower.

7. The process of claim 6 wherein said additive is added at a point between the bottom of said tower and the point where said crude oxide is fed to said tower.

* * * * *